United States Patent
Lei et al.

(10) Patent No.: US 11,654,437 B2
(45) Date of Patent: May 23, 2023

(54) ASSAY CARTRIDG FOR MOLECULAR DIAGNOSIS

(71) Applicant: QuanDx Inc., San Jose, CA (US)

(72) Inventors: Xiaojun Lei, San Jose, CA (US); Qian Xu, San Jose, CA (US)

(73) Assignee: QUANDX INC., San Jose, CA (US)

(*) Notice: Subject to any disclaimer, the term of this patent is extended or adjusted under 35 U.S.C. 154(b) by 42 days.

(21) Appl. No.: 16/660,819

(22) Filed: Oct. 23, 2019

(65) Prior Publication Data

US 2021/0121889 A1 Apr. 29, 2021

(51) Int. Cl.
*C12Q 1/6806* (2018.01)
*C12Q 1/686* (2018.01)
*B01L 7/00* (2006.01)
*B01L 3/00* (2006.01)

(52) U.S. Cl.
CPC ............. *B01L 7/525* (2013.01); *B01L 3/5027* (2013.01); *C12Q 1/686* (2013.01); *C12Q 1/6806* (2013.01); *B01L 2200/027* (2013.01); *B01L 2300/0816* (2013.01); *B01L 2300/0864* (2013.01); *B01L 2300/0867* (2013.01)

(58) Field of Classification Search
CPC ....... B01L 2200/027; B01L 2300/0816; B01L 2300/0864; B01L 2300/0867; B01L 3/5027; B01L 7/525; C12Q 1/6806; C12Q 1/686
See application file for complete search history.

(56) References Cited

U.S. PATENT DOCUMENTS

| 2009/0074624 | A1* | 3/2009 | Liang | B01L 3/502 422/400 |
| 2009/0298129 | A1* | 12/2009 | Spence | G01N 35/00732 901/30 |
| 2012/0122231 | A1* | 5/2012 | Tajima | G01N 35/026 436/164 |
| 2013/0130369 | A1* | 5/2013 | Wilson | G01N 35/1016 435/289.1 |
| 2015/0298120 | A1* | 10/2015 | Westberg | B01L 3/502 435/6.12 |
| 2018/0282786 | A1* | 10/2018 | Pugia | C12Q 1/6806 |

* cited by examiner

*Primary Examiner* — Young J Kim
(74) *Attorney, Agent, or Firm* — Jun He Law Offices P.C.; Yi Zhang

(57) ABSTRACT

The present disclosure provides an assay cartridge used in a PCR-based molecular diagnostic device. In one embodiment, the assay cartridge comprises (1) an elongated body having a proximal end, a distal end and a plurality of compartments arranged between the proximal end and the distal end, said plurality of compartments include at least a first pipette tip holder near the proximal end, and a second pipette tip holder near the distal end; and (2) a seal assembly covering the elongated body comprising a rigid frame which matches the top periphery of the elongated body, and an elastic top mounted on the rigid frame, the elastic top comprising a first sub-portion near the proximal end comprising a first ring structure that matches the first pipette holder, and a second sub-portion near the distal end comprising a second ring structure that matches the second pipette holder.

13 Claims, 9 Drawing Sheets

ASSAY CARTRIDG FOR MOLECULAR DIAGNOSIS

FIELD OF THE INVENTION

The present invention generally relates to devices and systems for molecular diagnostics.

BACKGROUND OF THE INVENTION

Many nucleic acid sequences have been used to diagnose and monitor disease, detect risk and decide which therapies will work best for individual patient. For example, the presence of nucleic acid sequences associated with infectious organisms may indicate an infection by the organism. The presence of an altered nucleic acid sequence in a patient sample may indicate activation or inactivation of a pathway related to a disease or disorders.

Detection of clinically related nucleic acid sequences in a sample generally involves isolating nucleic acid from the sample and amplification of specific nucleic acid sequences followed by detection of the amplified products. However, complexities of the multi-step process of isolating nucleic acid limit the processing flexibility and reduce the repeatability. For example, DNA and RNA have different chemical properties and stability, whose preparation requires different processing conditions. Further, samples from different source organism may require different steps to isolate nucleic acids. For example, isolating DNA from bacteria may use harsher conditions (e.g., higher temperature, higher concentration of detergent, etc.) than releasing DNA from relatively labile mammalian cells. Therefore, there is a need for an analytical system providing flexible and adjustable operating capabilities to meet the diverse demands of clinical diagnostics. Moreover, although amplification increases the sensitivity of the detection assay by providing sufficient copies of the specific nucleic acid sequences, it may risk erroneous results born of contamination. Therefore, there is also a need for an analytical system requiring minimal user participation to reduce contamination.

SUMMARY OF THE INVENTION

Embodiments of the present invention are directed to devices and systems associated with processing and analyzing samples for molecular diagnostics. Embodiments of the invention include an assay cartridge used in an automated, random access system for determining specific nucleic acid sequences in the sample.

In an aspect, the present disclosure provides an assay cartridge used in a molecular diagnostic device. In one embodiment, the assay cartridge comprises (1) an elongated body having a proximal end, a distal end and a plurality of compartments arranged between the proximal end and the distal end, said plurality of compartments include at least a first pipette tip holder near the proximal end, and a second pipette tip holder near the distal end; and (2) a seal assembly covering the elongated body comprising a rigid frame which matches the top periphery of the elongated body, and an elastic top mounted on the rigid frame, the elastic top comprising a first sub-portion near the proximal end comprising a first ring structure that matches the first pipette holder, and a second sub-portion near the distal end comprising a second ring structure that matches the second pipette holder.

In certain embodiments, the plurality of compartments further includes a sample loading well near the proximal end. In certain embodiments, the sample loading well is removable from the elongated body.

In certain embodiments, the plurality of compartments includes a purification well. In certain embodiments, the purification well contains magnetic microparticles capable of binding to nucleic acid.

In certain embodiments, the plurality of compartments includes at least a PCR reaction well near the distal end. In certain embodiments, the assay cartridge further comprises a slidable lid removably covering the PCR reaction well.

In certain embodiments, the elastic top is made of latex. In certain embodiments, the first sub-portion and/or the second sub-portion of the elastic top has a circular ripple structure.

In certain embodiments, the sealable assembly comprises an opening for loading a volatile reagent to a compartment of the elongated body. In certain embodiments, the volatile reagent is isopropanol.

In certain embodiments, the assay cartridge can be loaded into a cartridge carrier. In some embodiments, the cartridge carrier is capable of controlling the position of the assay cartridge when the assay cartridge loaded in the cartridge carriage is asserted into the molecular diagnostic device.

These and other features, aspects, and advantages of the present invention will become better understood with regard to the following description, appended claims and accompanying drawings.

DETAILED DESCRIPTION OF THE INVENTION

Figure 1:
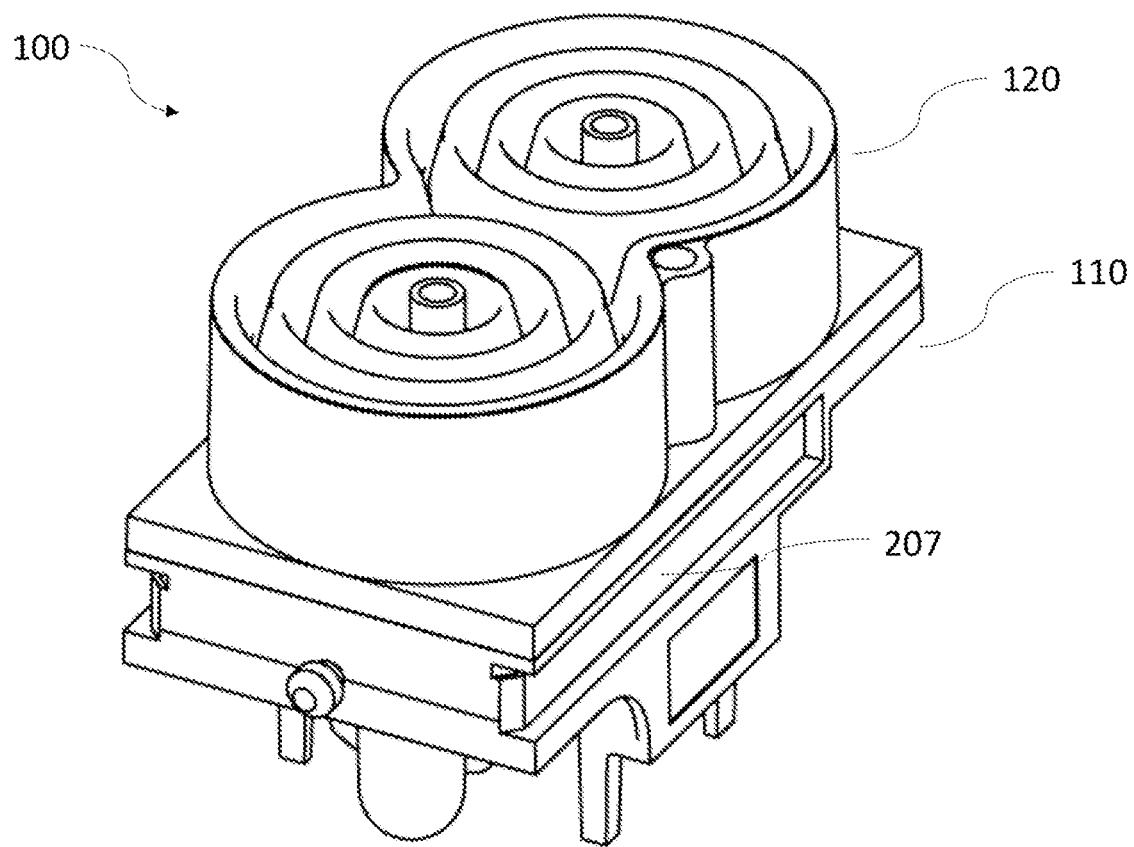
FIG. 1 shows a top perspective view of an assay cartridge according to an embodiment of the invention.

In the Summary of the Invention above and in the Detailed Description of the Invention, and the claims below, and in the accompanying drawings, reference is made to particular features (including method steps) of the invention. It is to be understood that the disclosure of the invention in this specification includes all possible combinations of such particular features. For example, where a particular feature is disclosed in the context of a particular aspect or embodiment of the invention, or particular claim, that feature can also be used, to the extent possible, in combination with and/or in the context of other particular aspects and embodiments of the invention, and in the invention generally.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

The term "comprises" and grammatical equivalents thereof are used herein to mean that other components, ingredients, steps, etc. are optionally present. For example, an article "comprising" (or "which comprises") components A, B, and C can consist of (i.e., contain only) components A, B, and C, or can contain not only components A, B, and C but also one or more other components.

Where reference is made herein to a method comprising two or more defined steps, the defined steps can be carried out in any order or simultaneously (except where the context excludes that possibility), and the method can include one or more other steps which are carried out before any of the defined steps, between two of the defined steps, or after all the defined steps (except where the context excludes that possibility).

Where a range of value is provided, it is understood that each intervening value, to the tenth of the unit of the lower limit unless the context clearly dictate otherwise, between the upper and lower limit of that range and any other stated or intervening value in that stated range, is encompassed within the disclosure, subject to any specifically excluded limit in the stated range. Where the stated range includes one or both of the limits, ranges excluding either or both of those included limits are also included in the disclosure.

It will be appreciated that for simplicity and clarity of illustration, where appropriate, reference numerals have been repeated among the different figures to indicate corresponding or analogous elements. In addition, numerous specific details are set forth in order to provide a thorough understanding of the embodiments described herein. However, the embodiments described herein can be practiced without the specific details. In other instances, methods, procedures and components have not been described in detail so as not to obscure the related relevant function being described. Also, the description is not to be considered as limiting the scope of the implementations described herein. It will be understood that descriptions and characterizations of the embodiments set forth in this disclosure are not to be considered as mutually exclusive, unless otherwise noted.

The following definitions are used in the disclosure:

The term "at least" followed by a number is used herein to denote the start of a range beginning with that number (which may be a range having an upper limit or no upper limit, depending on the variable being defined). For example, "at least 1" means 1 or more than 1. The term "at most" followed by a number is used herein to denote the end of a range ending with that number (which may be a range having 1 or 0 as its lower limit, or a range having no lower limit, depending upon the variable being defined). For example, "at most 4" means 4 or less than 4, and "at most 40%" means 40% or less than 40%. When, in this specification, a range is given as "(a first number) to (a second number)" or "(a first number)-(a second number)," this means a range whose lower limit is the first number and whose upper limit is the second number. For example, 25 to 100 mm means a range whose lower limit is 25 mm, and whose upper limit is 100 mm.

PCR or "Polymerase Chain Reaction" refers to a method used to amplify DNA through repeated cycles of enzymatic replication followed by denaturation of the DNA duplex and formation of new DNA duplexes. Denaturation and renaturation of the DNA duplex may be performed by altering the temperature of the DNA amplification reaction mixture. Reverse-transcriptase PCR (RT-PCR) refers to a PCR process including a step to transcribing RNA (e.g., mRNA) into cDNA which is then amplified. Real time PCR refers to a PCR process in which a signal that is related to the amount of amplified DNA in the reaction is monitored during the amplification process. This signal is often fluorescence. However, other detection methods are possible. In an exemplary embodiment, a PCR subsystem takes a prepared and sealed reaction vessel and performs a complete real time polymerase chain reaction analysis, thermal cycling the sample multiple times and reporting the intensity of emitted fluorescent light at each cycle.

Assay Cartridge

In one aspect, the present disclosure provides an assay cartridge used in a fully automated, random access device for determining specific nucleic acid sequences in samples. An example of the fully automated, random access system is disclosed in U.S. patent Ser. No. 10/427,162 to Lei et al., the disclosure of which is incorporated herein through reference. The system can combine two general functions: sample preparation in the form of isolating nucleic acids from a sample, and detection of specific sequences within the isolated nucleic acids. Toward this end, the assay cartridge used in the system has at least two distinct functional modules: one for process samples to isolate nucleic acids and a second for nucleic acid amplification and detection. In certain embodiments, the two functional modules are integrated into one unit. The system includes instrumentation that works on the assay cartridge to carry out the functions. In some embodiments, the instrumentation is contained in a single, enclosed device. The system also includes consumables incorporating necessary reagents for performance of a variety of assays and transfer devices (e.g., pipette tips). In certain embodiments, all consumables are contained in an assay cartridge so that there is no need to store any consumables in the device. The system may also include holders for samples, connections for power and information. These are integrated in a single unit to provide a system that performs major functions of sample handling, nucleic acid isolation, amplification and detection, and supporting functions such as supply and consumable management, information management and maintenance. In some embodiments, the system includes multiple assay cartridges, each of which can be processed independently and simultaneously, i.e., in a random access fashion.

Combining these functions into a single, highly automated, self-contained device provides seamless integration of molecular diagnostics into the workflow of the clinical laboratory. A further benefit is to perform all steps of nucleic acid determination to produce clinically acceptable results without the need for user intervention. The device allows users to load samples as they are available, and to perform determination on these samples based on the needs of the patients and physicians, without constraints on sample or analyte order being imposed by the system.

The assay cartridge disclosed herein can work with a seal assembly to provide a sealed space in which sample preparation and target sequence detection are carried out. Such arrangement to the most extent prevents cross contamination.

In certain embodiments, the assay cartridge comprises a sample preparation module and a PCR module. The sample preparation module is for purifying nucleic acids (e.g., genomic DNA, total RNA, etc.) from a sample (e.g., FFPE specimen, blood or saliva, etc.). The PCR module is for amplifying a target region in the purified nucleic acids. In certain embodiments, the sample preparation module and the PCR module are formed in one body that is functionally divided into a sample preparation module and a PCR module. In certain embodiments, the elongated body can be in the form a monolithic body and may be formed of plastic (or any other suitable material). In certain embodiments, the elongated body is made by a plastic injection molding process. Alternatively, the elongated body is made by assembling individual components into a rigid framework.

FIG. 1 shows an assay cartridge used for molecular diagnostic devices according to one embodiment of the invention. Referring to FIG. 1, the assay cartridge 100 includes an elongated body 110 formed to include multiple compartments, which may hold fluids (e.g., reagents) and devices (e.g., pipette tips) needed to process various samples. Examples of compartments may include one or more sample loading wells, one or more purification wells, one or more reagent storage wells and one or more pipette tip holders. The assay cartridge 100 further includes a seal assembly 120 that covers the elongated body and prevents cross contamination.

Figure 2:
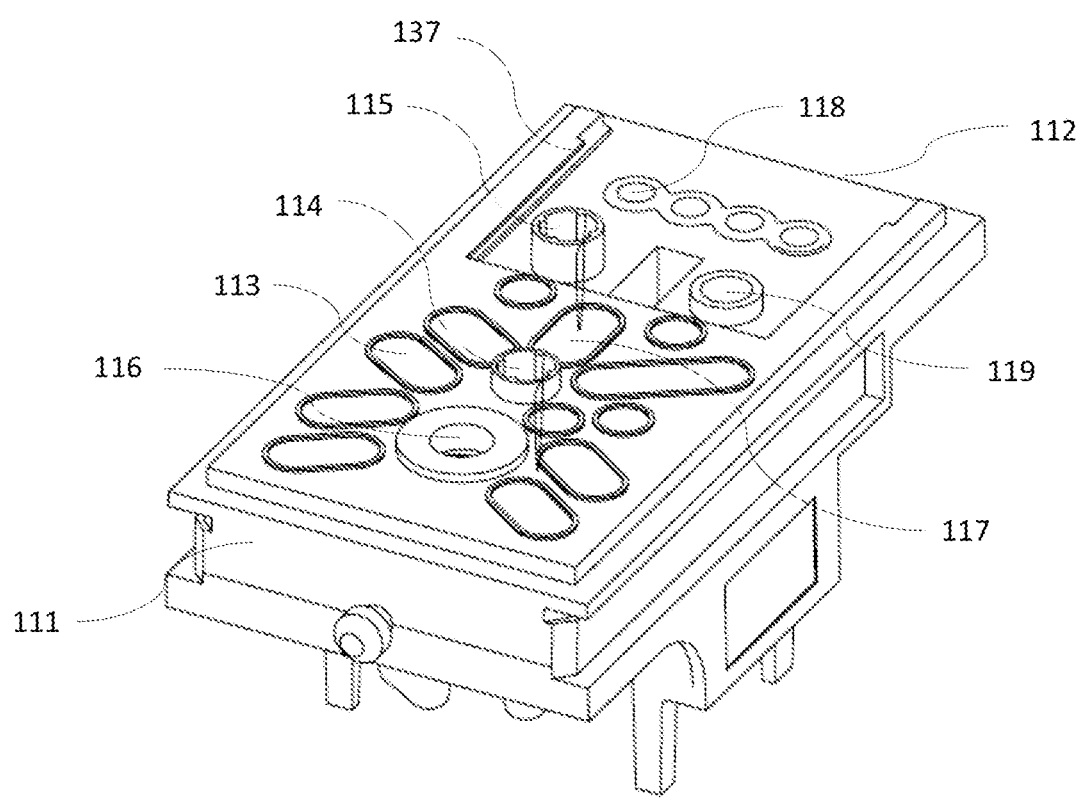
FIG. 2 shows a top perspective view of the body of an assay cartridge according to one embodiment of the invention.

FIG. 2 shows the elongated body of an assay cartridge used for molecular diagnostic devices according to one embodiment of the invention. Referring to FIG. 2, the elongated body 110 includes a proximal end 111, a distal end 112, and a plurality of compartments 113 between the proximal end 111 and the distal end 112 at opposite ends of the elongated body 110. The orientation of the compartments defines the top and bottom portion of the assay cartridge 100. Typically, the compartments are open at the top and closed on the bottom and sides.

In certain embodiments, the plurality of compartments can be divided into several sub-regions, each of which has one pipette tip holder. Referring to FIG. 2, the elongated body 110 includes a first pipette tip holder 114 near the proximal end 111. The elongated body 110 further includes a second pipette tip holder 115 near the distal end 112.

Figure 3:
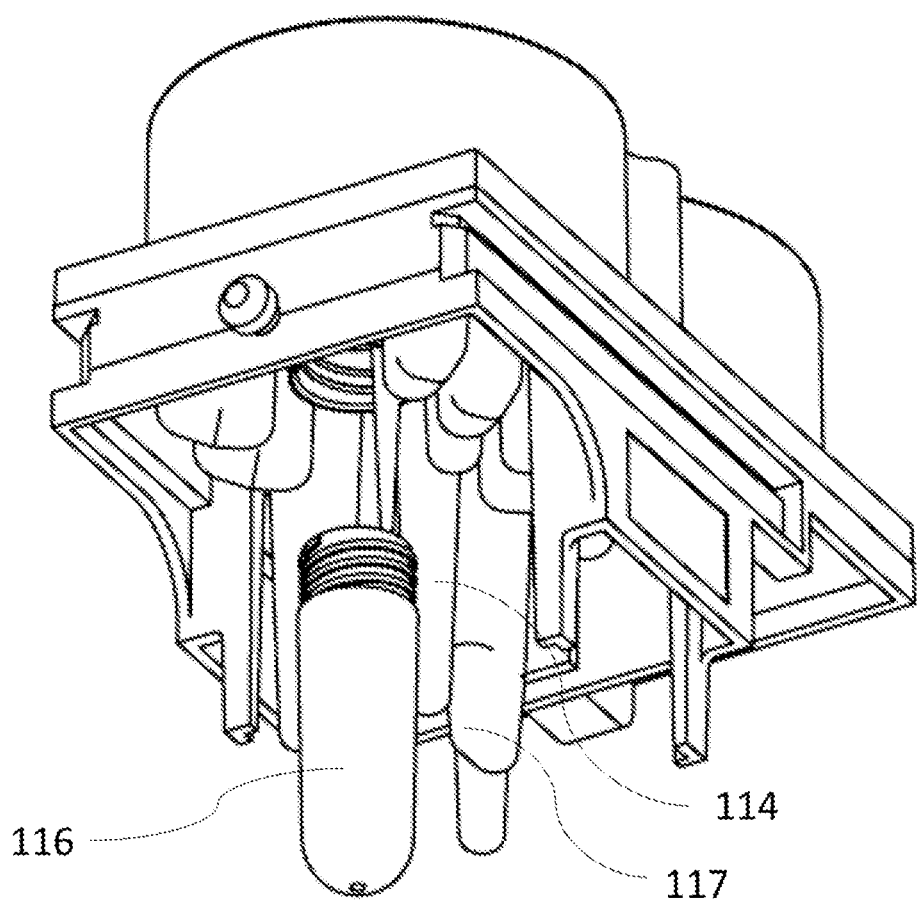
FIG. 3 shows a bottom perspective view of an assay cartridge according to one embodiment of the invention.

In certain embodiments, the sub-regions generally match the sample preparation module located near the proximal end 111, and the PCR module located near the distal end 112, each including compartments to carry out the corresponding functions of the module. Referring to FIG. 2, the elongated body 110 includes a sample loading well 116 located near the proximal end 111 and the first pipette tip holder 114. The sample loading well 116 has a shape designed to contain a relatively large reaction volume, to permit effective mixing of its contents, and to permit aspiration with minimal dead volume. In certain embodiments, the sample loading well 116 is cylindrical with conically tapered bottoms. This shape minimizes dead volume and allows a pipettor to collect all, or nearly all, of the contained reagent. In certain embodiments, the sample loading well 116 has a volume of about 1000 to 2000 microliters. In certain embodiments, the sample loading well 116 is detachable from the elongated body 110 (see FIG. 3). The sample can be added to the sample loading well 116 before attached to the assay cartridge and loaded in the molecular diagnostic device. In certain embodiments, the sample loading well 116 contains lysis buffer for effectively lysing the sample.

Referring to FIG. 2, the elongated body 110 also includes a purification well 117 located near the proximal end 111 and the first pipette tip holder 114. In certain embodiments, the purification well 117 is cylindrical with conically tapered bottoms. This shape minimizes dead volume and allows a pipettor to collect all, or nearly all, of the contained reagent. In some embodiments, the purification well 117 may hold the solid phase microparticles (e.g., magnetic nanoparticles). In some embodiments, the purification well 117 stores solid phase microparticles in suspension, but dry storage may extend shelf life. In either case, solid phase microparticles may require mixing before use either to resuspend microparticles that settle in storage or to disperse a rehydrated suspension.

While the device operates on other compartments in the assay cartridge primarily from the top, the purification well 117 can also interact with a magnet through its sides and edges (e.g., the bottom). In certain embodiments, when the assay cartridge is loaded into the device and the solid phase microparticles need to be collected, a magnet is pushed up to contact closely to the purification well. The magnet can be controlled to set up a magnetic field that collects and pellets magnetically responsive microparticles on the wall of the purification well. The magnet can be turned off (i.e., to remove the magnetic field) when needed so that the magnetically responsive microparticles can be mixed with other contents in the purification well 117 or be collected by a pipettor. In certain embodiments, when needed, the magnet stays at a home position that is low on the bottom to avoid affecting the solid phase microparticle in the purification well.

In one embodiment, to isolate DNA or RNA from a sample that has been lysed in the sample loading well 116, proper binding buffer is added to allow DNA or RNA to bind to magnetically responsive microparticles. A magnet is then pushed up to contact closely to the purification well 117 to apply the magnet field and collect the microparticles on one side of the purification well 117. The liquid is removed using the pipettor system. The magnet field is then removed and the wash buffer is added into the purification well and fully mixed with the microparticles. The magnet field is again applied to collect the microparticles and the wash buffer is removed. Elution buffer is added to the purification well 117 to mix with the microparticles. Purified DNA or RNA is then eluted from the microparticles for downstream application.

As shown in FIG. 2, the compartments near the proximal end 111 and the first pipette tip holder 114 can be arranged as a radiation pattern such that a tip loaded in the pipette tip holder 114 can easily access to the compartments with the operation of a dispense system in a molecular diagnostic device, which includes a pipettor for transferring reagents between compartments (see, e.g., U.S. patent Ser. No. 10/427,162, the disclosure of which is incorporated herein by reference). Certain compartments are reagent storage wells that hold discrete components used in the extraction and purification process, including cell lysis buffer, wash buffer and elute buffer. Reagent storage wells may be of various sizes and shapes. In certain embodiments, to facilitate the operation of magnet working with the purification well 117, certain reagent storage wells have depth smaller than the purification well 117.

As shown in FIG. 2, the elongated body 110 further includes near the distal end 112 and the second pipette tip holder 115, PCR wells 118 and a mixing well 119 for storing and mixing the purified nucleic acids with PCR reagents.

In some embodiments, various compartments in the elongated body 110 lack common walls to prevent the creeping of liquids between compartments. This has the benefit of reducing the possibility of contamination between compartments. In some embodiments, the external profile of each compartment closely tracks the cavity internal profile, i.e., the walls of the compartment can be of relatively constant thickness and can be thin compared to the size of the compartment. One of the benefits of such design is to reduce the amount of material used and hence reduces the manufacturing cost of the module.

Seal Assembly

In certain embodiments, the assay cartridge described herein includes a seal assembly that covers the elongated body and prevents cross contamination. As described in details below, the seal assembly has a design that allows the assay cartridge to work with a dispense system in a molecular diagnostic device, which includes a pipettor for transferring reagents between compartments in the elongated body (see, e.g., U.S. patent Ser. No. 10/427,162, the disclosure of which is incorporated herein by reference).

Figure 4:
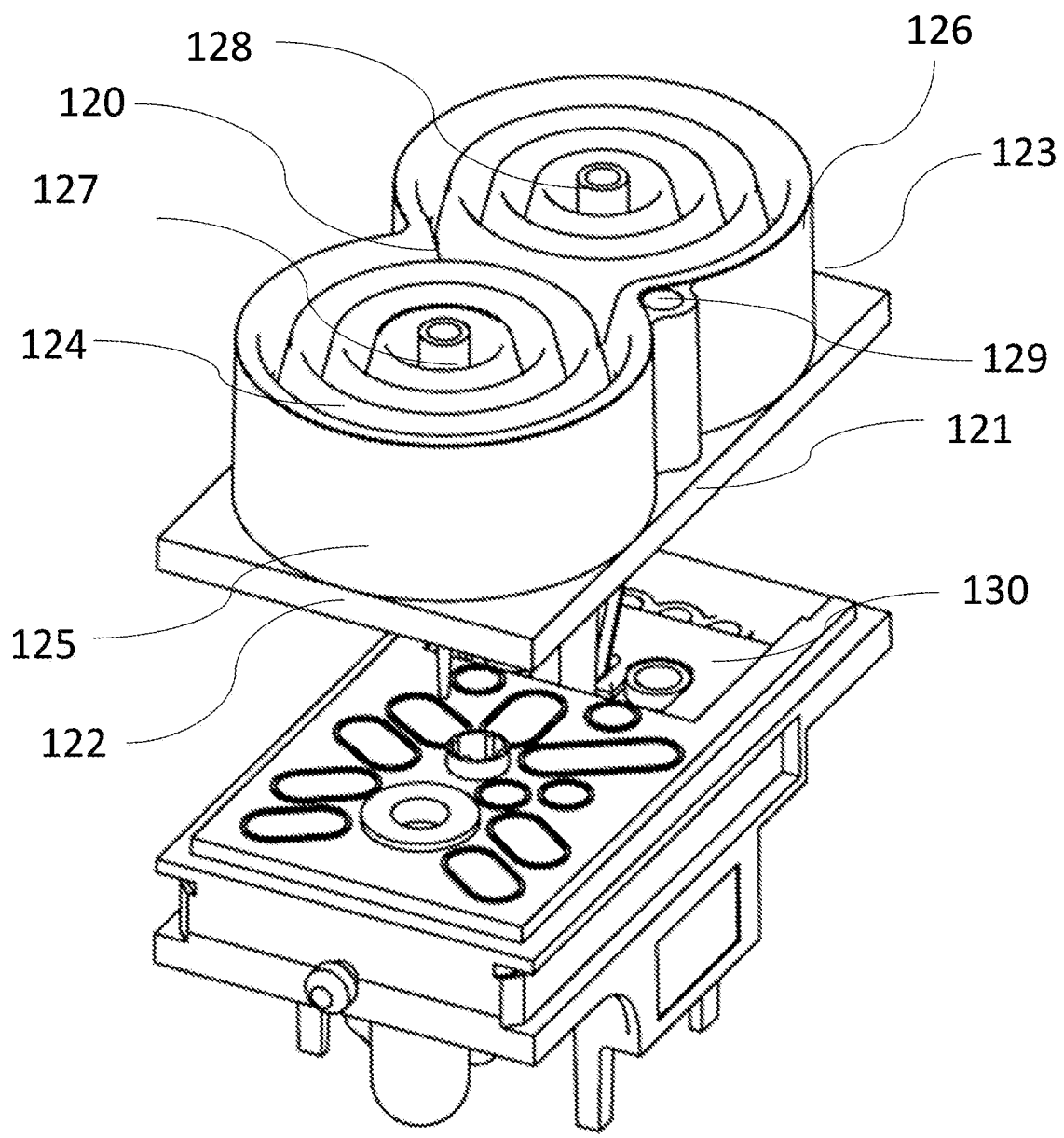
FIG. 4 shows a top view of a seal assembly detached from the body of an assay cartridge according to one embodiment of the invention.

FIG. 4 shows a top perspective view of a seal assembly according to one embodiments of the present invention. Referring to FIG. 4, the seal assembly 120 contains a rigid frame 121 that matches the top periphery of the elongated body and has a proximal end 122 and a distal end 123. The seal assembly 120 further includes an elastic top 124 mounted on the rigid frame 121. The elastic top 124 contains a flexible film that can be stretched in various directions. The flexible film can be made of any elastic materials. In certain embodiments, the flexible film is made of latex.

In some embodiments, the elastic top 124 contains multiple sub-portions. Referring to FIG. 4, the elastic top 124 contains a first sub-portion 125 near the proximal end 122 and a second sub-portion 126 near the distal end 123. The first and the second sub-portions generally have a round shape. In certain embodiments, each of the first and the second sub-portions has a circular ripple structure. The first sub-portion 125 at the center of the circular ripple includes a first ring structure 127 structure that matches the first pipette tip holder 114 in the elongated body when the seal assembly covers the elongated body. The second sub-portion 126 at the center of the circular ripple includes a second ring structure 128 that matches the second pipette tip holder 115 in the elongated body when the seal assembly covers the elongated body. Such design allows the pipettor and the dispense system of the molecular diagnostic device to maneuver pipette tips through the ring structure. The flexibility of the film allows the pipette tips to move between various compartment of the assay cartridge without opening the sealed space.

In certain embodiments, the sealable assembly 120 further comprises an opening 129 for loading a volatile reagent to a compartment of the elongated body. In certain embodiments, the volatile reagent includes ethanol or isopropanol.

Dividing the assay cartridge into sub-regions, working together with the seal assembly, allows the automated, random access device to process the samples and carry out the detection in a sealed space using the pipette tips loaded in the pipette tip holder. In short, the seal assembly has a flexible film that covers the top portion of the assay cartridge. The seal assembly further includes ring structures in the flexible film that allows the pipettor and dispense system of the automated molecular diagnostic device to access and maneuver the pipette tips (for details of an example of the pipettor and dispense, see U.S. patent Ser. No. 10/427,162). The elasticity and flexibility of the film allows the pipette tips to move within the sealed space without detaching the seal assembly from the assay cartridge.

Slidable Lid

In one embodiment, the assay cartridge also contains a slidable lid that can cover the PCR reaction well after the reagents for PCR reaction are mixed and added to the PCR reaction well.

Figure 5A:
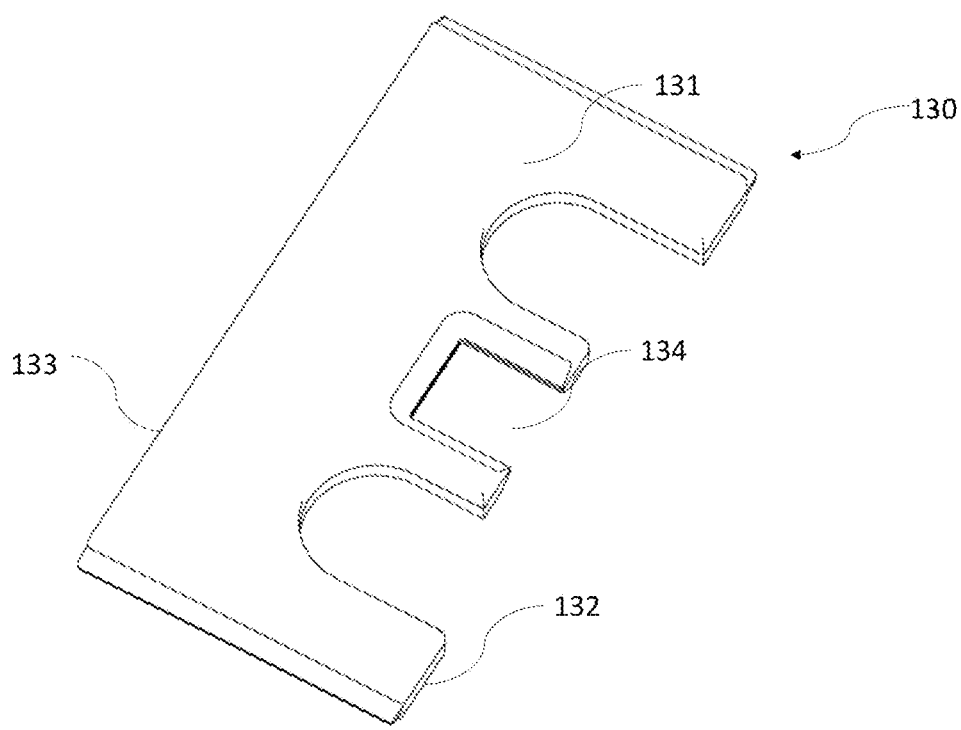
FIG. 5A shows a top perspective view of a slidable lid according to one embodiment of the invention.

FIG. 5A shows a top perspective view of a slidable lid 130 according to one embodiment of the invention. Referring to FIG. 5A, the slidable lid 130 includes a slab 131 having a proximal end 132 and a distal end 133. The slab 131 has a notch 134 near the proximal end 132.

Figure 5B:
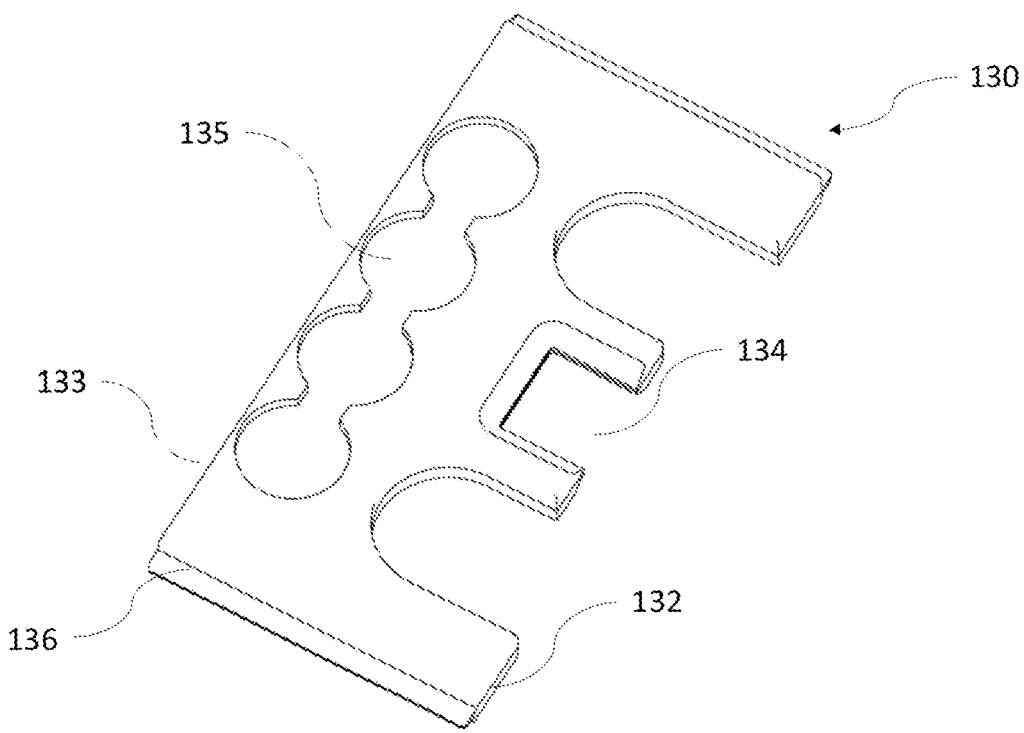
FIG. 5B shows a bottom perspective view of a slidable lid according to one embodiment of the invention.

FIG. 5B shows a bottom perspective view of the slidable lid 130 according to one embodiment. Referring to FIG. 5B, the slidable lid 130 has a convex element 135 near the distal end 133 that is resiliently attached to the slab 131. The convex element 135 has a spherical surface that is capable of covering a PCR reaction well of the assay cartridge. In some embodiments, the convex element has a height of 0.3-1.5 mm, e.g., about 0.3, 0.4, 0.5, 0.6, 0.7, 0.8, 0.9, 1.0, 1.1, 1.2, 1.3, 1.4 or 1.5 mm.

In some embodiments, the slab 131 has at least a pair of ridges 136 on the sides of the slab, said ridges matching a pair of grooves in the elongated body of the assay cartridge (see FIG. 2 137) and allowing the slidable lid 130 to slide along the grooves.

In some embodiments, the assay cartridge contains a wedge structure used to control the position of the slidable lid. The wedge structure locates adjacent to the notch 134 when the slab 131 is inserted to the groove 137. The wedge structure can be pushed towards the down side of the assay cartridge and is configured to push the slidable lid 130 to move towards the distal end when the wedge structure is pushed down.

In some embodiments, the bottom of the slab 131 has a distance of about 0-0.5 mm from the top surface of the PCR module when the slidable lid 130 is mounted to the assay cartridge. As such, the convex element is refrained from extending downwards by the top surface of the PCR module. When the slidable lid 130 is pushed to the distal end of the assay cartridge and slides to a close position, the resilient convex element 135 extends downwards to the PCR reaction well and seals the PCR reaction well.

Cartridge Carriage

Figure 6A:
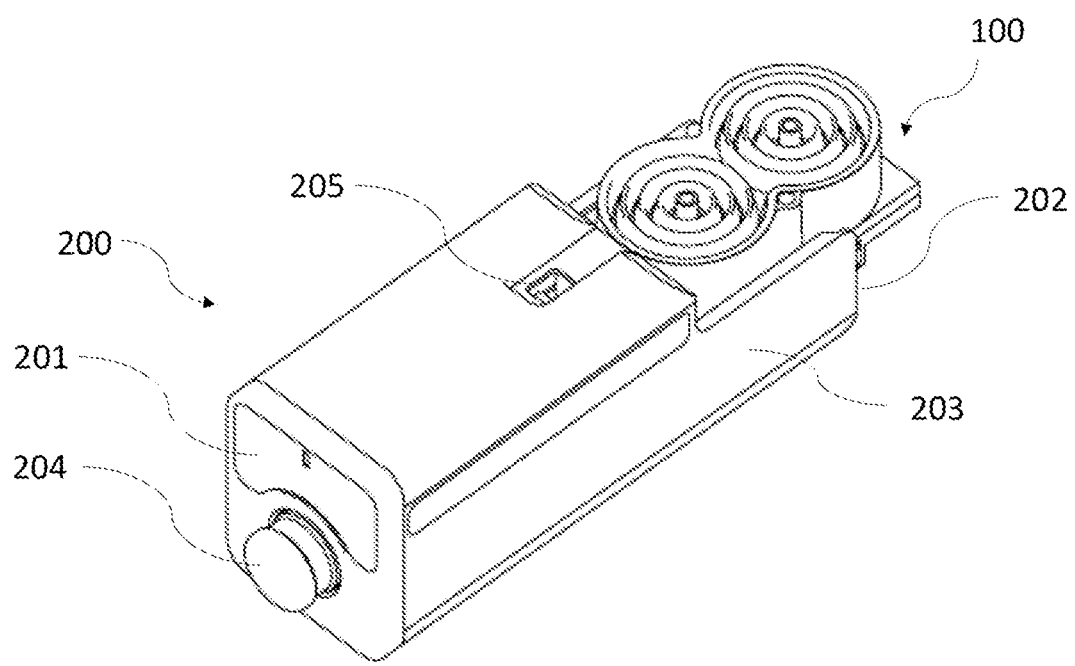
FIG. 6A shows a top perspective view of an assay cartridge loaded into a cartridge carrier according to one embodiment of the invention.
Figure 6B:
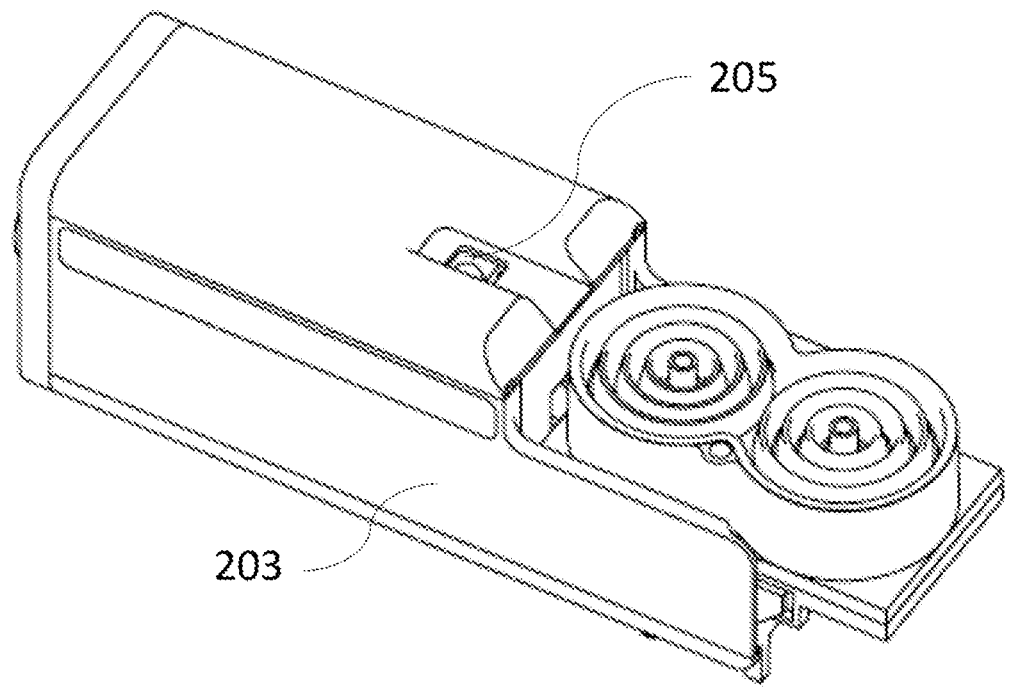
FIG. 6B shows a top perspective view of an assay cartridge loaded into a cartridge carrier according to one embodiment of the invention.

To work within the automated system, the assay cartridge described herein can be loaded in a cartridge carriage (described below) before being inserted into the automated molecular diagnostic device. FIGS. 6A and 6B each shows a top perspective view of a cartridge carriage according to an embodiment of the invention, with an assay cartridge loaded in the cartridge carriage. Referring to FIGS. 6A and 6B, the cartridge carriage 200 includes an elongated body having a proximal end 201, a distal end 202, and a pair of side walls 203 that together defines a cavity configured to hold the assay cartridge when the assay cartridge 100 is loaded into the cartridge carriage. In one embodiment, the PCR reaction wells of the assay cartridge are not loaded into the cavity. This design allows the PCR reaction wells to be received in the receptacles of the thermal cycler module of the molecular diagnostic device.

Figure 7A:
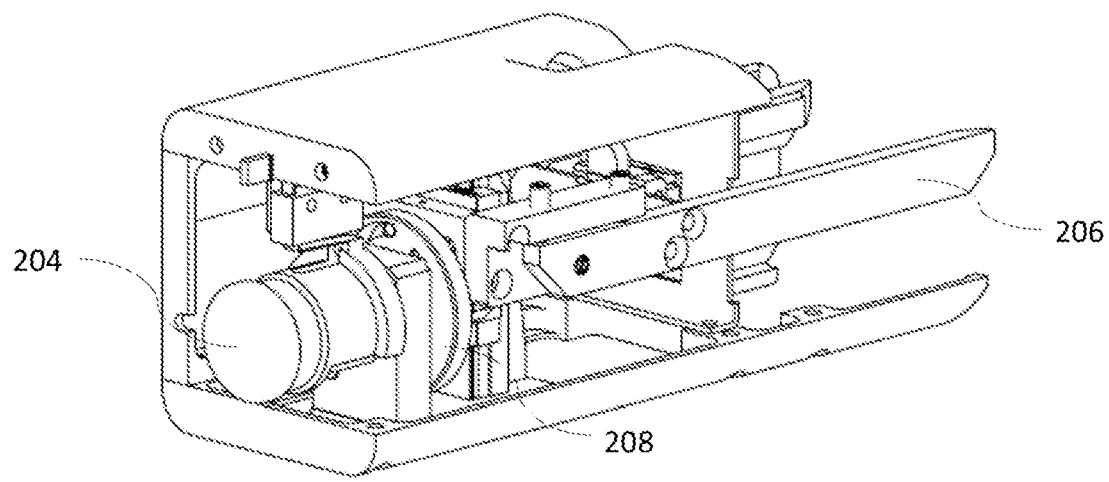
FIG. 7A shows a perspective view of a cartridge carriage according to an embodiment of the invention.
Figure 7B:
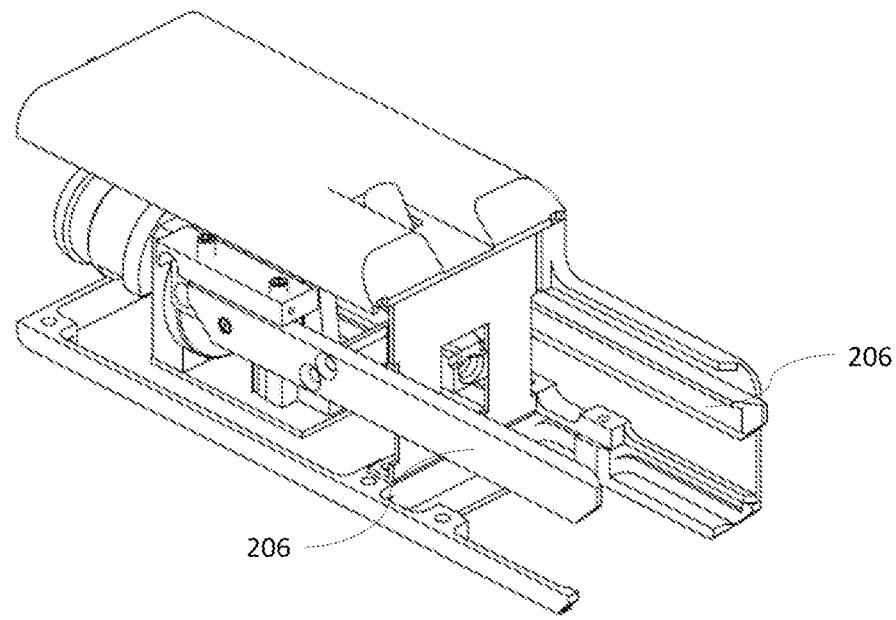
FIG. 7B shows a perspective view of a cartridge carriage according to an embodiment of the invention.

The cartridge carriage 200 includes a control assembly with a control button 204 that can control the position of the assay cartridge 100 when the assay cartridge is inserted in the automated system. FIGS. 7A and 7B each shows a perspective view of a cartridge carriage according to an embodiment of the invention, in which a side wall 203 is removed to dismantle the control assembly. Referring to FIGS. 7A and 7B, the control assembly includes a control button 204 that can be rotated and pushed. The control button 204 connects to a round plate 208 through an axis. The rotation of the round plate 208 raises or lowers a pair of bars 206, which can slide to a pair of grooves 207 in the elongated body of an assay cartridge (see FIG. 1).

Figure 8:
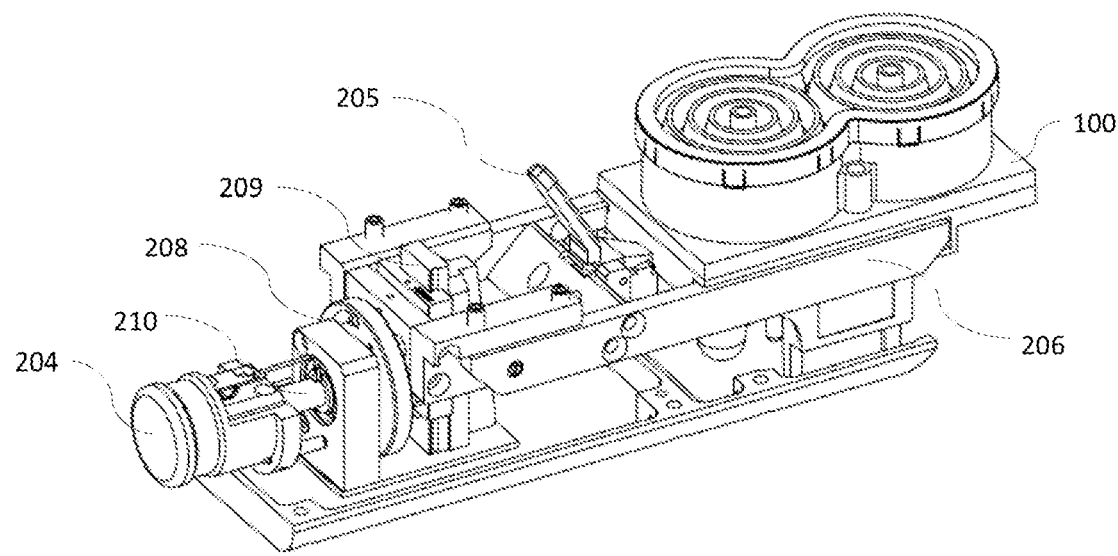
FIG. 8 shows a perspective view of a cartridge carriage according to an embodiment of the invention, in which an assay cartridge is loaded and the control assembly is exposed.

FIG. 8 shows a perspective view of a cartridge carriage according to an embodiment of the invention, in which an assay cartridge is loaded and the control assembly is exposed. Referring to FIG. 8, after an assay cartridge 100 is loaded to the cartridge carriage through a pair of bars 206, a lock button 205 can lock the assay cartridge 100 in the cartridge carriage. The control assembly includes a control button 204 that controls the rotation of a round plate 208 through an axis 210. The rotation of the round plate 208 raises or lowers a guide 209, which raises or lowers the pair of bars 206.

Figure 9:
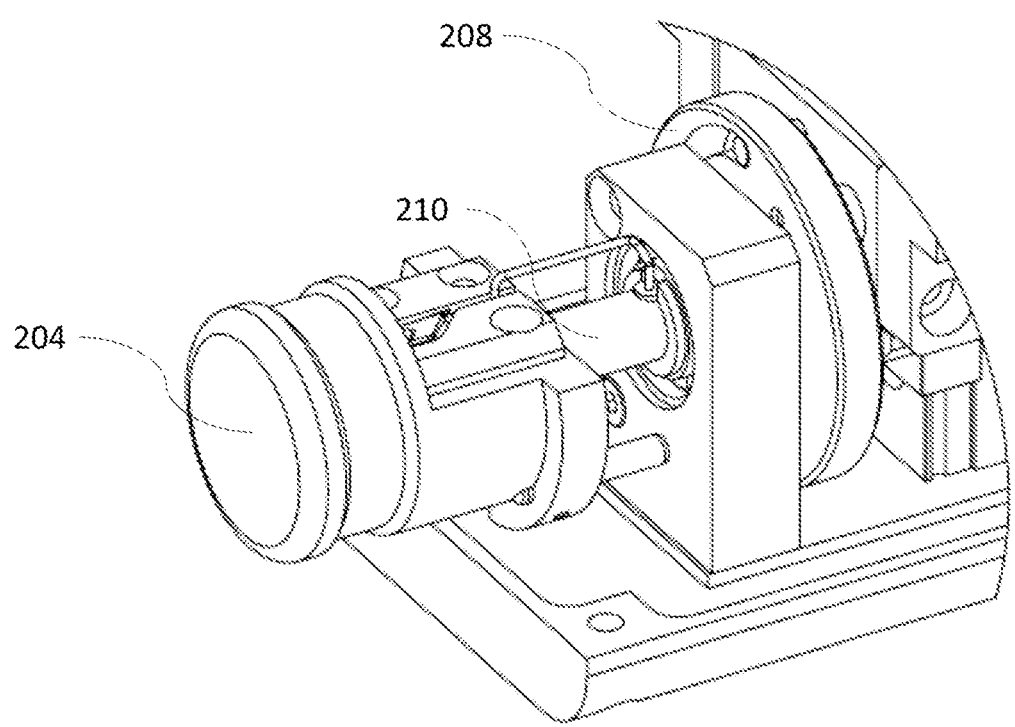
FIG. 9 shows an enlarged perspective view of the control assembly of a cartridge carriage according to an embodiment of the invention.

FIG. 9 shows an enlarged perspective view of the control assembly of a cartridge carriage according to an embodiment of the invention, in which the control button 204, the axis 210 and the round plate 208 are shown.

Figure 10:
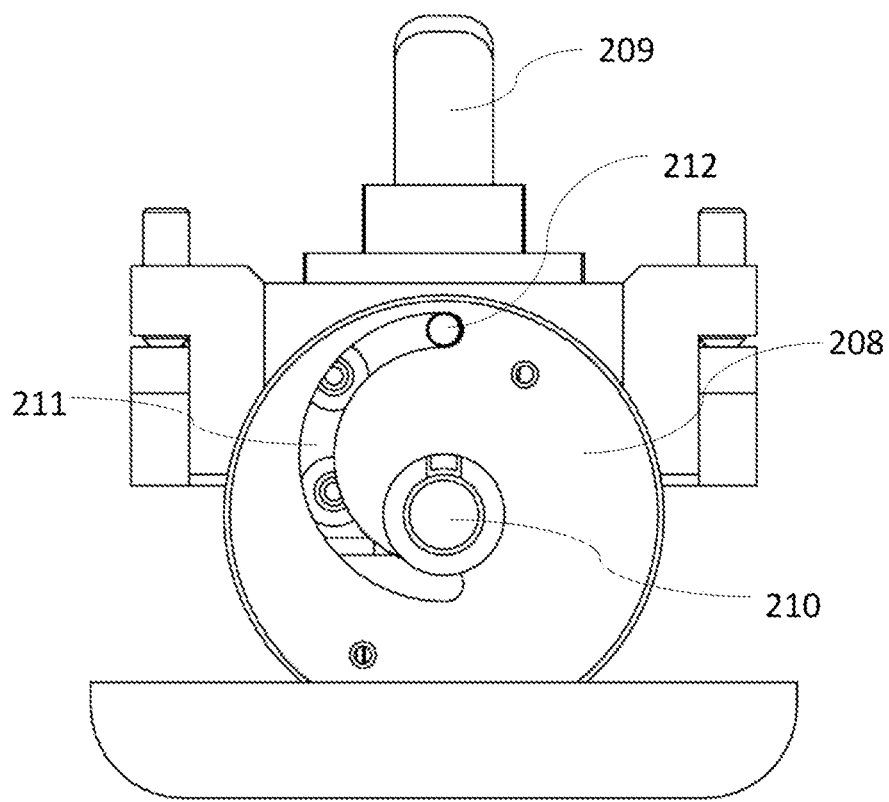
FIG. 10 shows a front view of a round plate connected to a guide according to an embodiment of the invention.

FIG. 10 shows a front view of a round plate connected to a guide according to an embodiment of the invention. Referring to FIG. 10, a round plate 208 is connected to a control button (not shown) through an axis 210. The round plate 208 has an eccentric arc groove 211, in which a pin 212 is inserted. The pin 212 links to a guide 209, which is connected to the pair of bars 206 (not shown). The moving of the pin 212 in the eccentric arc groove 211 raises (when the round plate 208 rotates counter clockwise) or lowers (when the round plate 208 rotates clockwise) the guide 209, thus raising or lowering the bars 206.

The previous description provides exemplary embodiments only, and is not intended to limit the scope, applicability, or configuration of the disclosure. Rather, the previous description of the exemplary embodiments will provide those skilled in the art with an enabling description for implementing one or more exemplary embodiments. It is understood that various changes may be made in the function and arrangement of elements without departing from the spirit and scope of the invention. Several embodiments were described herein, and while various features are ascribed to different embodiments, it should be appreciated that the features described with respect to one embodiment may be incorporated within other embodiments as well. By the same token, however, no single feature or features of any described embodiment should be considered essential to every embodiment of the invention, as other embodiments of the invention may omit such features.

Specific details are given in the previous description to provide a thorough understanding of the embodiments. However, it will be understood by one of ordinary skill in the art that the embodiments may be practiced without these specific details. For example, circuits, systems, networks, processes, and other elements in the invention may be shown as components in block diagram form in order not to obscure the embodiments in unnecessary detail. In other instances, well-known circuits, processes, algorithms, structures, and techniques may be shown without unnecessary detail in order to avoid obscuring the embodiments.

While detailed descriptions of one or more embodiments have been give above, various alternatives, modifications, and equivalents will be apparent to those skilled in the art without varying from the spirit of the invention. Moreover, except where clearly inappropriate or otherwise expressly noted, it should be assumed that the features, devices, and/or components of different embodiments may be substituted and/or combined. Thus, the above description should not be taken as limiting the scope of the invention. Lastly, one or more elements of one or more embodiments may be combined with one or more elements of one or more other embodiments without departing from the scope of the invention.

What is claimed is:

1. An assay cartridge used in a PCR-based molecular diagnostic device, comprising
   (1) an elongated body having a proximal end, a distal end and a plurality of compartments arranged between the proximal end and the distal end, said plurality of compartments includes at least
      a first pipette tip holder near the proximal end, and
      a second pipette tip holder near the distal end; and
   (2) a seal assembly covering the elongated body comprising
      a rigid frame which matches the top periphery of the elongated body, and
      an elastic top mounted on the rigid frame, the elastic top comprising
         a first sub-portion near the proximal end comprising a first ring structure that matches the first pipette holder, and
         a second sub-portion near the distal end comprising a second ring structure that matches the second pipette holder,
      wherein the compartments near the proximal end and the first pipette tip holder are arranged as a radiation pattern;
      wherein the first sub-portion and/or the second sub-portion of the elastic top has a circular ripple structure; and
      wherein the plurality of compartments further includes at least a PCR reaction well near the distal end, and the assay cartridge further comprises a slidable lid removably covering the PCR reaction well.

2. The assay cartridge of claim 1, wherein the plurality of compartments includes a sample loading well near the proximal end.

3. The assay cartridge of claim 2, wherein the sample loading well is removable from the elongated body.

4. The assay cartridge of claim 1, wherein the plurality of compartments includes a purification well.

5. The assay cartridge of claim 4, wherein the purification well contains magnetic microparticles capable of binding to nucleic acid.

6. The assay cartridge of claim 1, wherein the elastic top is made of latex.

7. The assay cartridge of claim 1, wherein the sealable assembly comprises an opening for loading a volatile reagent to a compartment of the elongated body.

8. The assay cartridge of claim 7, wherein the volatile reagent includes ethanol or isopropanol.

9. An assay cartridge assembly, comprising:
   the assay cartridge of claim 1; and
   a cartridge carrier which loads the assay cartridge.

10. The assay cartridge assembly of claim 9, wherein the cartridge carrier comprises a cavity configured to hold the assay cartridge when the assay cartridge is loaded into the cartridge carrier.

11. The assay cartridge assembly of claim 10, wherein the at least a PCR reaction well near the distal end of the assay cartridge is not within the cavity when the assay cartridge is fully loaded into the cartridge carrier.

12. The assay cartridge assembly of claim 9, wherein the cartridge carrier comprises a control assembly that controls the position of the assay cartridge when the assay cartridge loaded in the cartridge carrier is inserted into the PCR-based molecular diagnostic device.

13. The assay cartridge assembly of claim 12, wherein the control assembly comprises:
   a control button,
   a round plate connected to the control button via an axis, wherein the round plate comprises an eccentric arc groove; and
   a guide connected to the round plate via a pin, wherein the pin is inserted in the eccentric arc groove.

\* \* \* \* \*